United States Patent
Spinelli et al.

(10) Patent No.: US 11,583,598 B2
(45) Date of Patent: Feb. 21, 2023

(54) SANITIZATION ASSEMBLY, SHELF FOR FURNISHING ELEMENT WITH SANITIZATION ASSEMBLY AND FURNISHING ELEMENT WITH SANITIZATION ASSEMBLY

(71) Applicant: POLIFORM S.P.A., Inverigo (IT)

(72) Inventors: Alberto Spinelli, Inverigo (IT); Aldo Spinelli, Inverigo (IT); Giovanni Anzani, Inverigo (IT)

(73) Assignee: POLIFORM S.P.A., Como (IT)

( * ) Notice: Subject to any disclaimer, the term of this patent is extended or adjusted under 35 U.S.C. 154(b) by 59 days.

(21) Appl. No.: 16/838,273

(22) Filed: Apr. 2, 2020

(65) Prior Publication Data

US 2020/0316237 A1    Oct. 8, 2020

(30) Foreign Application Priority Data

Apr. 5, 2019  (IT) .......... 102019000005256

(51) Int. Cl.
*A61L 2/26*    (2006.01)
*A61L 2/08*    (2006.01)
(Continued)

(52) U.S. Cl.
CPC .............. *A61L 2/088* (2013.01); *A47B 47/03* (2013.01); *A47B 96/021* (2013.01); *A61L 2/14* (2013.01);
(Continued)

(58) Field of Classification Search
CPC ......... A47B 47/03; A47B 96/021; A61L 2/08; A61L 2/088; A61L 2/10; A61L 2/14;
(Continued)

(56) References Cited

U.S. PATENT DOCUMENTS

| 9,011,780 B1 | 4/2015 | Burnett |
|---|---|---|
| 9,066,988 B1 | 6/2015 | Burnett |

(Continued)

FOREIGN PATENT DOCUMENTS

| CN | 205456858 U | 8/2016 | |
|---|---|---|---|
| KR | 20170036437 A | 4/2017 | |
| WO | WO-2013058346 A1 * | 4/2013 | ............. A47B 61/00 |

OTHER PUBLICATIONS

Machine Translation of WO 2013/058346 (Year: 2013).*

(Continued)

*Primary Examiner* — Timothy C Cleveland
(74) *Attorney, Agent, or Firm* — Armstrong Teasdale LLP (57) ABSTRACT

Described herein is a sanitization assembly including: a sanitization device, such as for example a photocatalytic device or ionizer or the like; and a containment element. The sanitization device is received in the containment element, and the containment element includes a box-shaped, box-like containment body. The box-like containment body includes side containment body surfaces and has dimensions in the width and thickness thereof that are substantially the same as those of a panel or rack or shelf of a furnishing element that includes side shelf surfaces. The box-like containment body can be assembled on the panel or rack or shelf, thus being continuous with the panel or rack or shelf. The side shelf surfaces substantially continue in the side containment body surfaces.

14 Claims, 11 Drawing Sheets

(51) Int. Cl.
*A47B 47/03* (2006.01)
*A47B 96/02* (2006.01)
*A61L 2/14* (2006.01)

(52) U.S. Cl.
CPC ..... *A61L 2202/122* (2013.01); *A61L 2202/26* (2013.01)

(58) Field of Classification Search
CPC ... A61L 2/202; A61L 2/24; A61L 2/26; A61L 2202/122; A61L 2202/26
See application file for complete search history.

(56) References Cited

U.S. PATENT DOCUMENTS

| | | | |
|---|---|---|---|
| 9,098,823 B2 * | 8/2015 | Slesinger | A47B 96/021 |
| 9,205,169 B1 | 12/2015 | Burnett | |
| 9,593,861 B1 | 3/2017 | Burnett | |
| 9,782,510 B1 | 10/2017 | Burnett | |
| 2019/0022262 A1 * | 1/2019 | Andrews | A45C 15/00 |

OTHER PUBLICATIONS

English translation of Italian Search Report and Written Opinion for Italian Patent Application No. 102019000005256, dated Jan. 13, 2020.12 pages.
https://www.youtube.com/watch?v=CXtmvQF79Ts; "Discover Lerna Air Cleaning System", 42 seconds, published by Casarredo; screencapture provided, as accessed Mar. 31, 2020.

* cited by examiner

SANITIZATION ASSEMBLY, SHELF FOR FURNISHING ELEMENT WITH SANITIZATION ASSEMBLY AND FURNISHING ELEMENT WITH SANITIZATION ASSEMBLY

CROSS-REFERENCE TO RELATED APPLICATIONS

This application claims the benefit of priority to Italian Patent Application No. 102019000005256, filed Apr. 5, 2019, the entire contents of which are hereby incorporated by reference herein.

FIELD OF THE INVENTION

The object of the present invention is a sanitization assembly, a shelf for a furnishing element with sanitization assembly and a furnishing element with sanitization assembly, as well as a method for sanitizing a compartment of a furnishing element.

BACKGROUND

Sterilants or sanitizers are known to be used to sanitize ambients. However, these solutions, which in certain cases are also quite accurate, are very costly and unsuitable for a daily use, for example for sanitizing a contained ambient such as a compartment of a wardrobe, and in particular for sanitizing the items and garments arranged therein.

There are also known sanitization devices for ambients based on photocatalytic technologies or ionizers or the like.

Solutions of this type are, for example, disclosed in U.S. Pat. Nos. 9,782,510, 9,593,861, 9,011,780, 9,205,169, 9,066,988.

Likewise, it is known to use these devices in reduced volumes such as wardrobes, to sanitize the garments or footwear when they are arranged therein. An example is disclosed, for example in this video https://www.youtube.com/watch?v=CXtmvQF79Ts.

This solution introduces an air purification device based on the photocatalytic technology, which is hung to the upper panel of the piece of furniture.

Although satisfactory from many perspectives, this solution is highly bulky and requires a significant flow rate to sanitize a compartment such as a wardrobe, which in any case risks not all areas being reached as they are divided by garments in the wardrobe, unless over very long periods of time.

Thus, the need is strongly felt to have a sanitization which allows the air flow emitted by the sanitization device to quickly reach the various items of clothing or items arranged in the furnishing element while at the same time being compact, not very bulky, and especially highly flexible in the configuration so as to quickly adapt to changes of the spaces of the wardrobe, for example by increasing or decreasing the space dedicated to very long items of clothing or partitioning the spaces with several shelves for putting away garments which are supported and not hung, or shoes or handbags or the like.

SUMMARY OF THE INVENTION

These and other objects are achieved by means of a sanitization assembly, a furnishing element shelf or sanitizing shelf, a furnishing element, as well as a method for sanitizing a compartment of a furnishing element, as described herein.

Certain advantageous embodiments are the subject of the dependent claims.

It has emerged from the analysis of this solution how the solution proposed allows increased efficiency to be obtained in the sanitization effect, especially due to the possibility of positioning the sanitization device close to the garments to be sanitized. Further, the solution proposed, also by virtue of the dimension thereof contained within the volume of a shelf (remaining within the standard dimensions of a shelf, for example of a wardrobe) allows the device also to be arranged below the garments or between one pile and the other of garments resting on the shelves, thus approaching the device and making it effective more quickly.

In particular, the solution proposed is highly flexible and adaptable to different configurations in a same furnishing element, making it also possible for the individual user to create his/her sanitization ambient adapted to the different wardrobe, by also changing it for each season.

BRIEF DESCRIPTION OF THE FIGURES

Further features and advantages of the invention will be apparent from the following description of preferred and non-limiting embodiments thereof, with reference to the accompanying drawings, in which.

DETAILED DESCRIPTION

Figure 1:
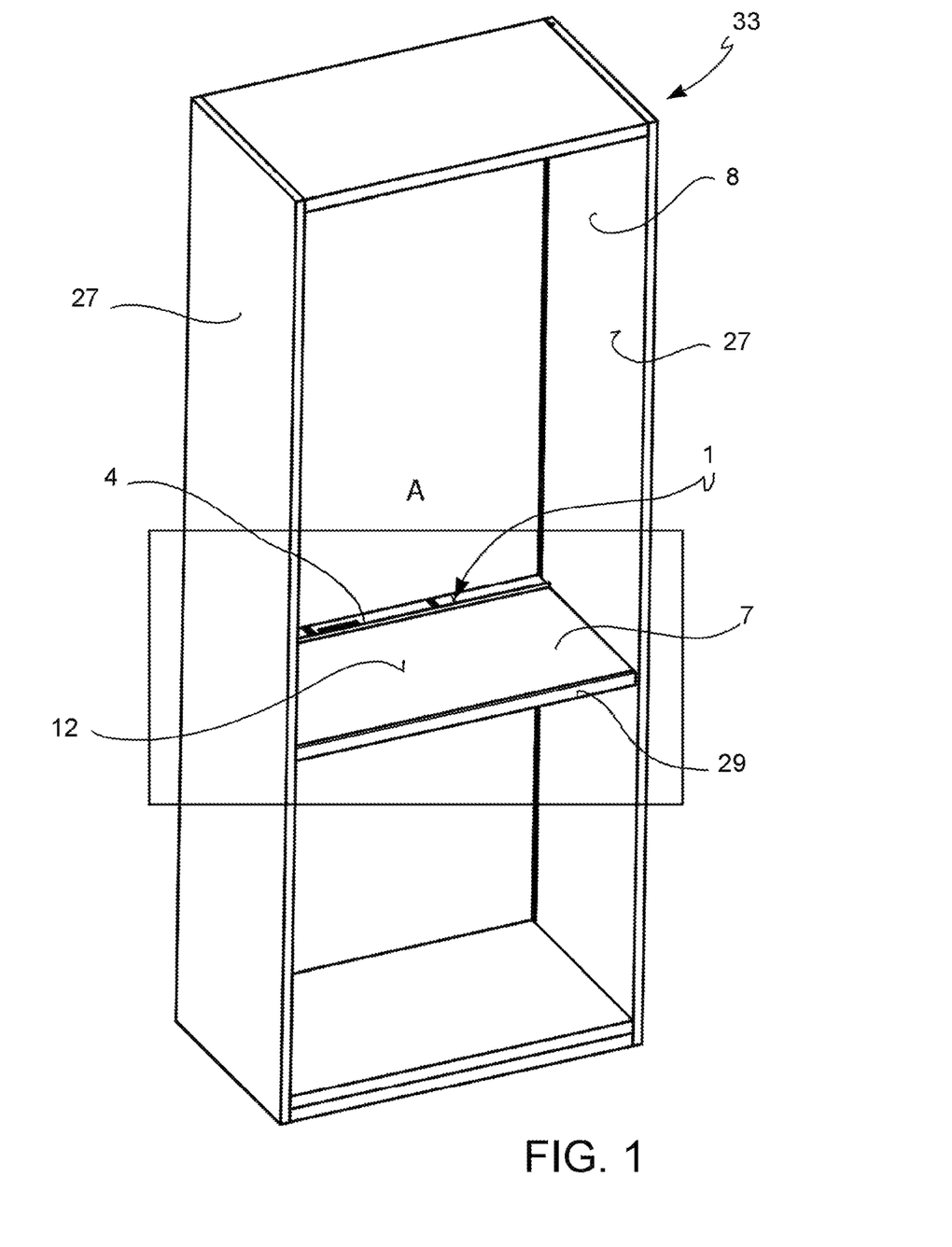
FIG. 1 shows an axonometric view of a structure of a furnishing element, here a container, for example a wardrobe, without closing shutters and wherein only a shelf is indicated for clarity of disclosure.
Figure 2:
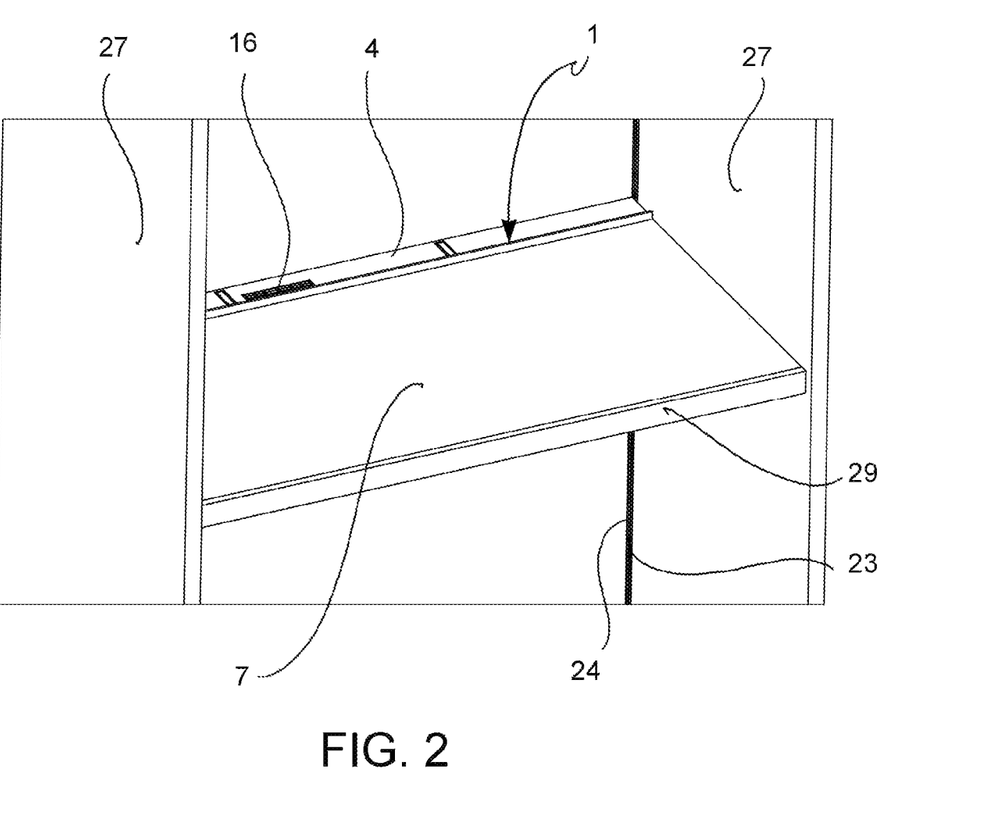
FIG. 2 shows an axonometric view of the circled detail A in FIG. 1.
Figure 3:
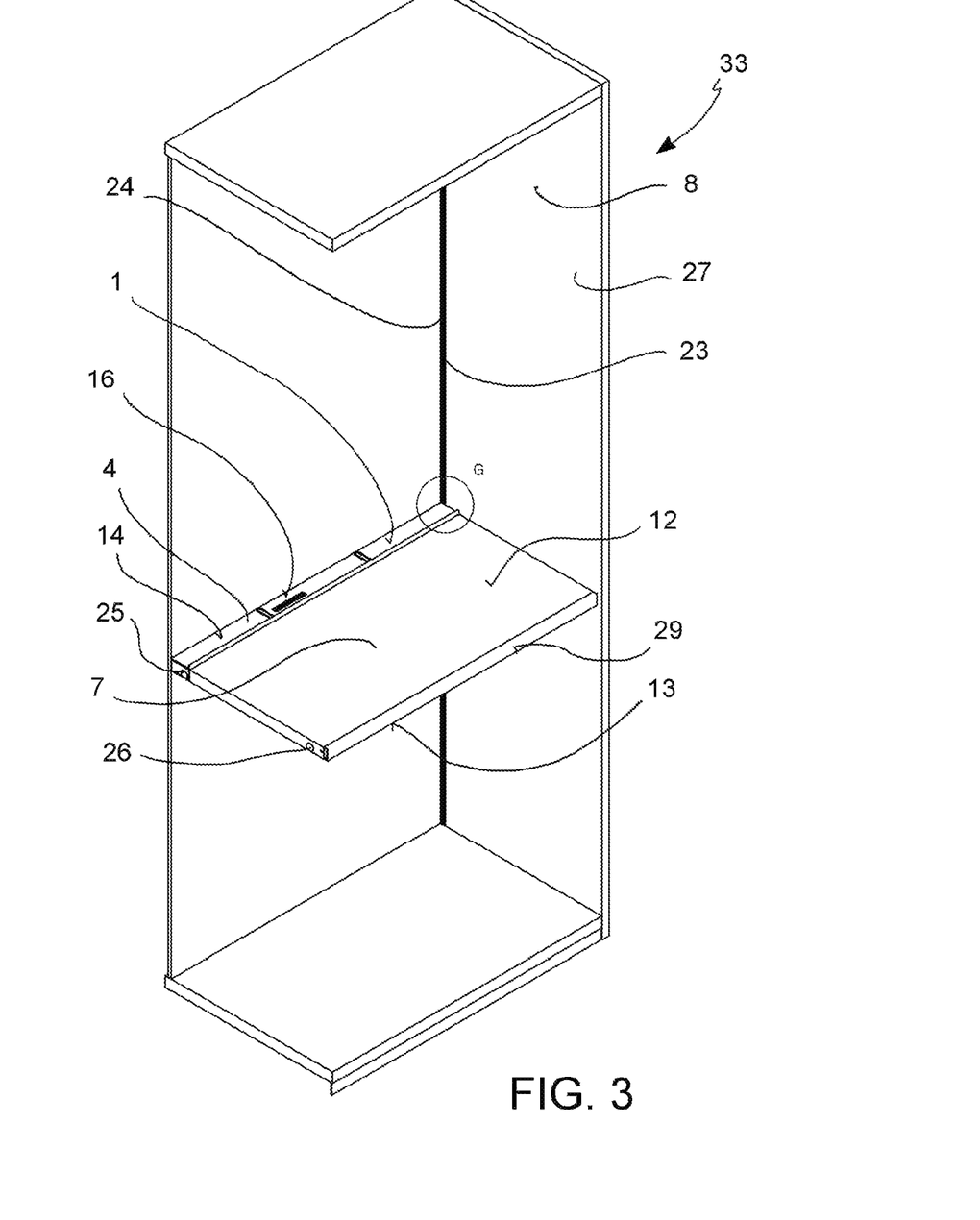
FIG. 3 shows an axonometric view of the structure in FIG. 1, wherein one of the side shoulders was removed to better note the details of the shelf.
Figure 4:
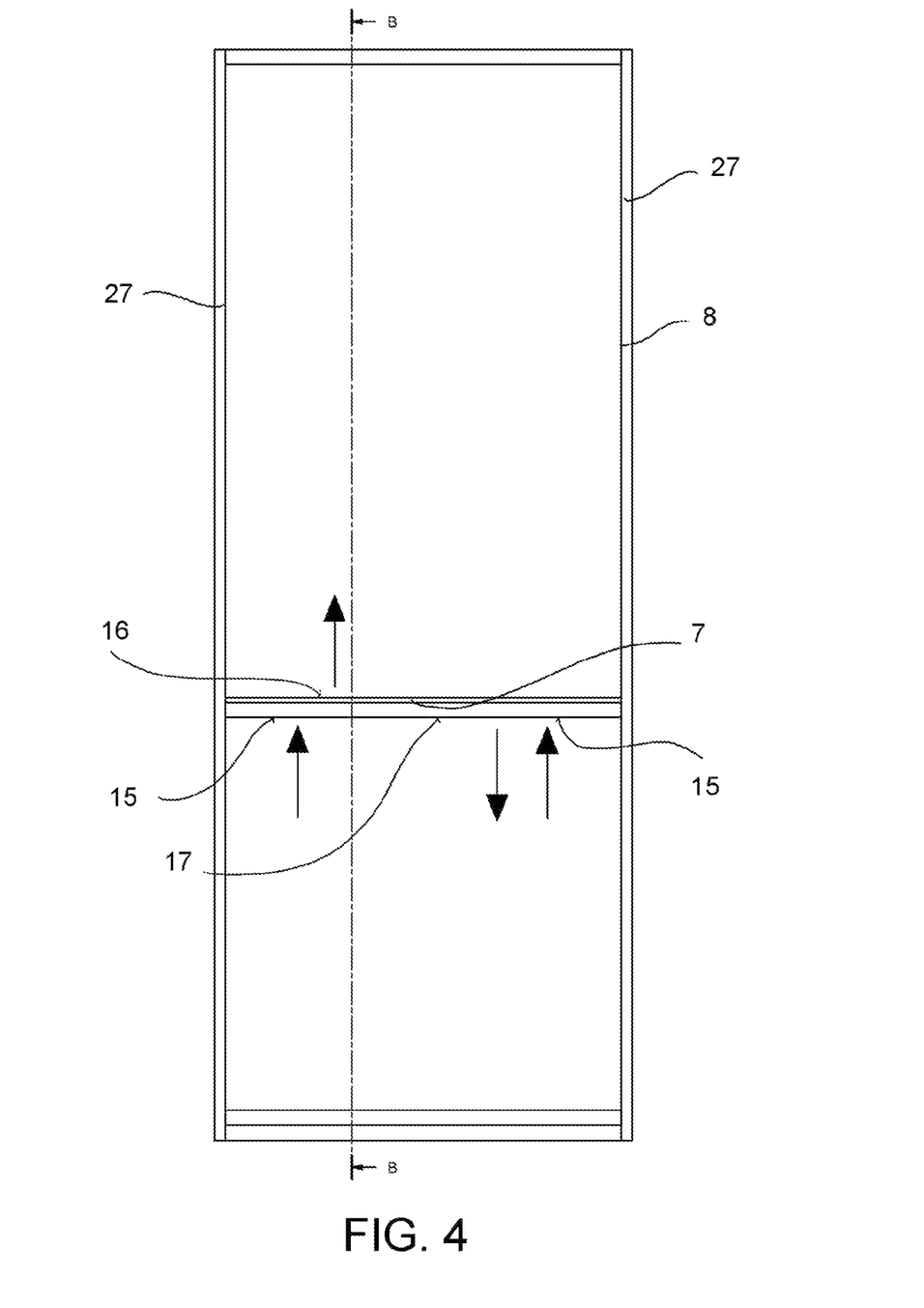
FIG. 4 shows a front view of the structure in FIG. 1, wherein the air flows are noted close to the sanitization device placed to be associated with and behind the shelf.
Figure 5:
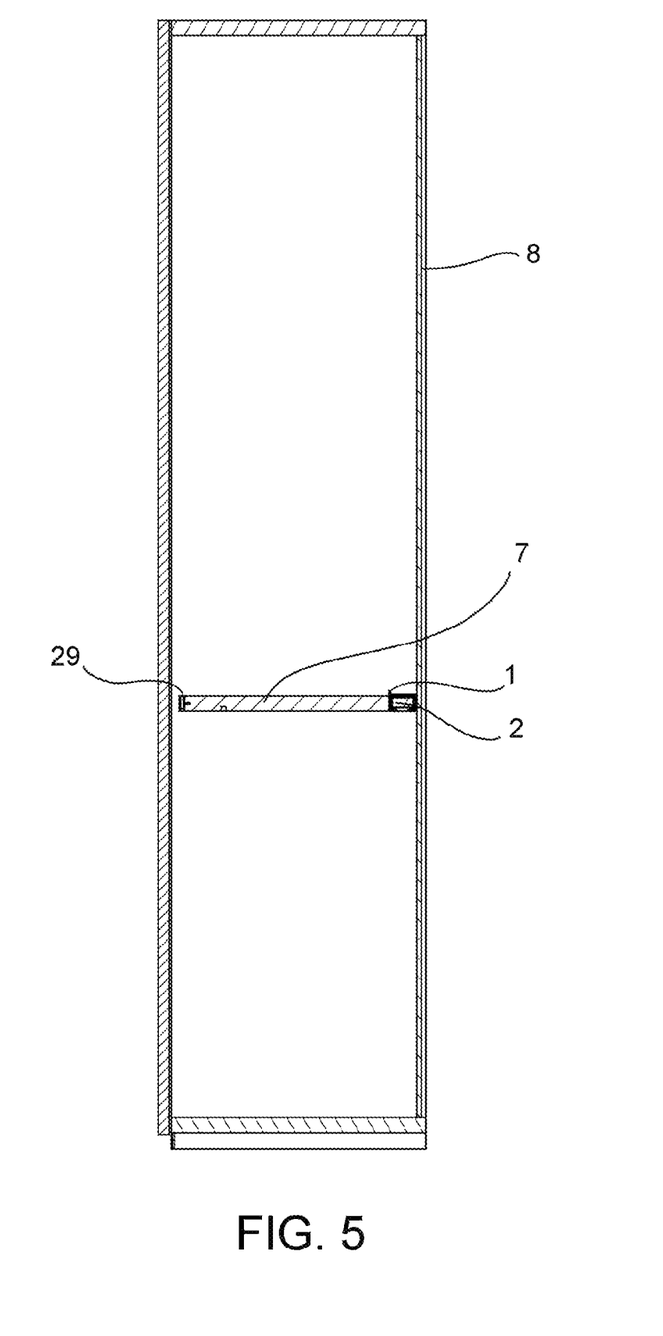
FIG. 5 shows a section of the structure in FIG. 1 according to line B-B in FIG. 4.
Figure 6:
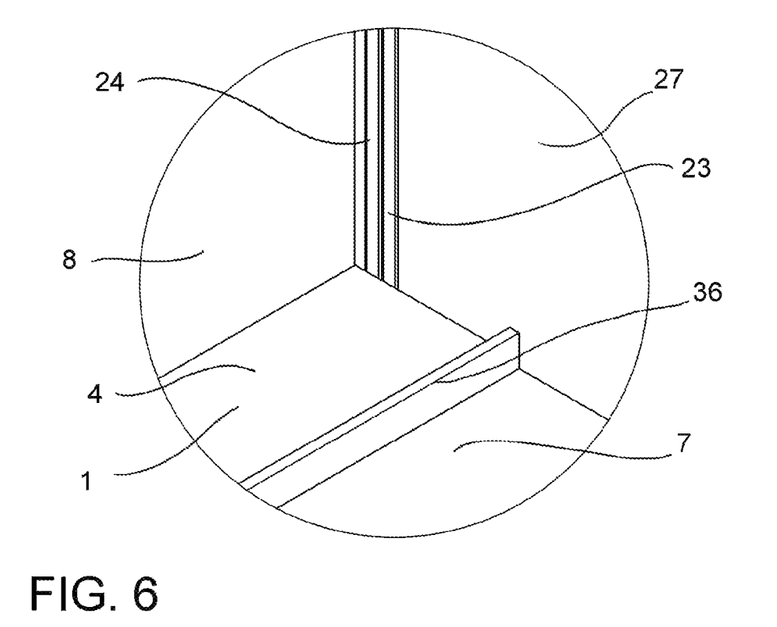
FIG. 6 shows an axonometric view of the details indicated with G in FIG. 3.
Figure 7:
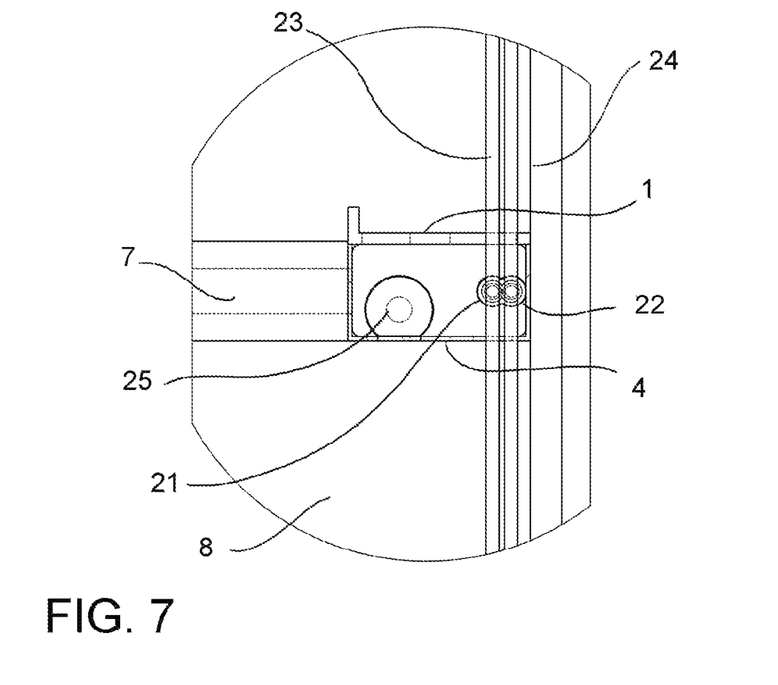
FIG. 7 shows a side view of a detail of the shelf in FIG. 1 associated with a shoulder of the furnishing element structure, where the shoulder is shown in transparency by emphasizing the electrified tracks which are accommodated here, and noting how the sanitization assembly with the electrical connector pins thereof engages said tracks to feed the sanitization device in any position in height the shelf is positioned in the compartment of the furnishing element structure.
Figure 8:
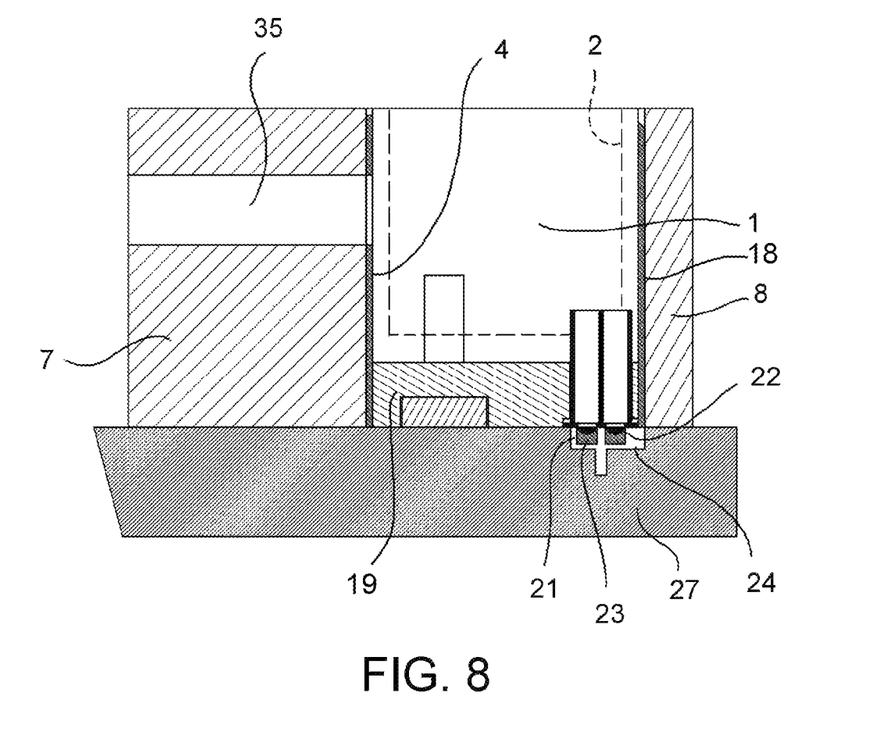
FIG. 8 shows a second section of the shelf in FIG. 1, according to a horizontal plane, noting a detail of the sanitization assembly where it is mechanically and electrically connected to the furnishing element shoulder and in the passageway for bringing the connection to the sanitization device control element arranged in the front edge of the shelf.
Figure 9:
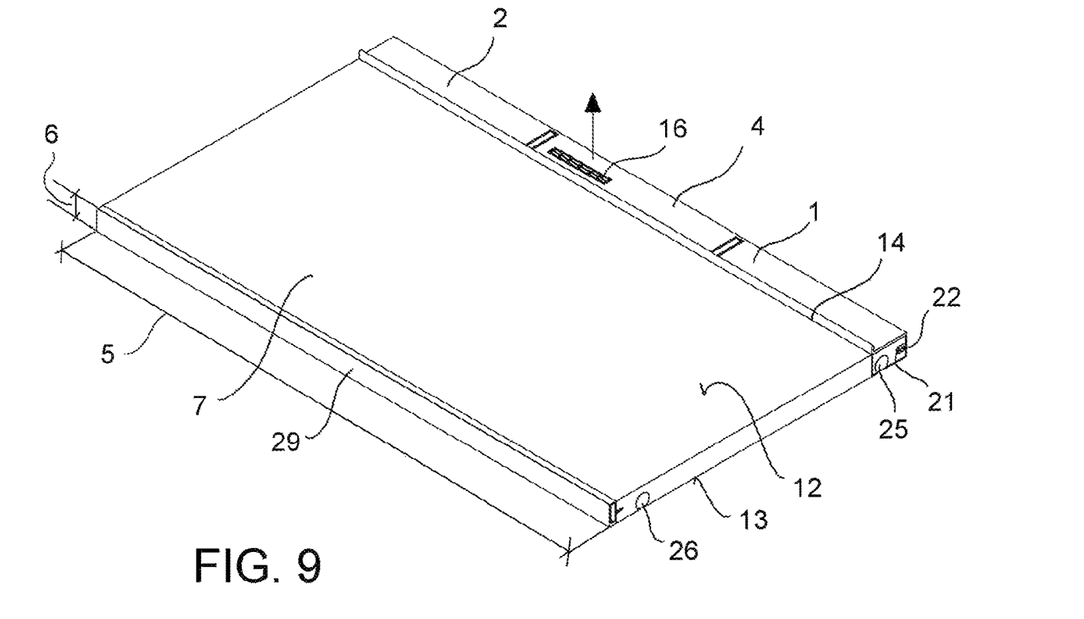
FIGS. 9 and 10 show axonometric views from the top and bottom of a shelf noting the air flows into and out of the sanitization assembly integrated in the shelf.
Figure 10:
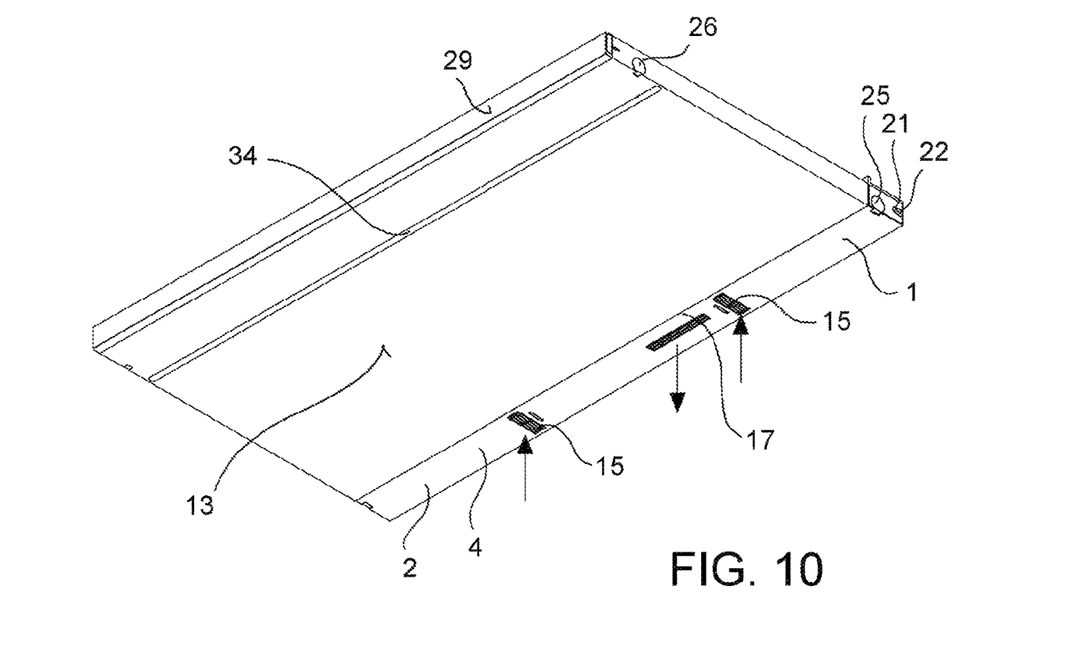
Figure 11:
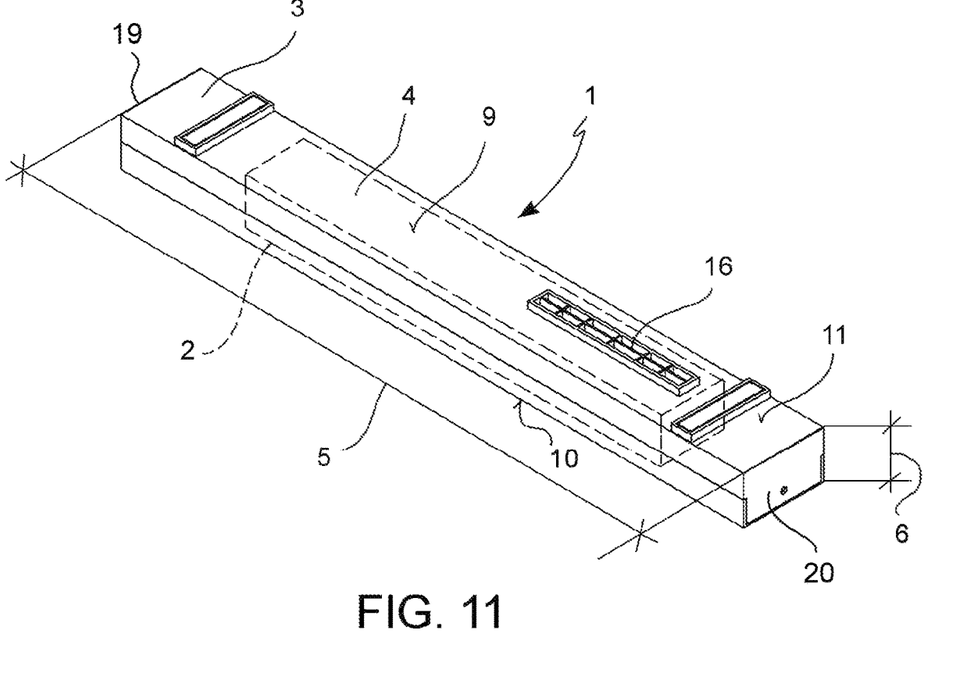
FIG. 11 shows an axonometric view of a sanitization assembly separated from the shelf with which it can be associated.
Figure 12:
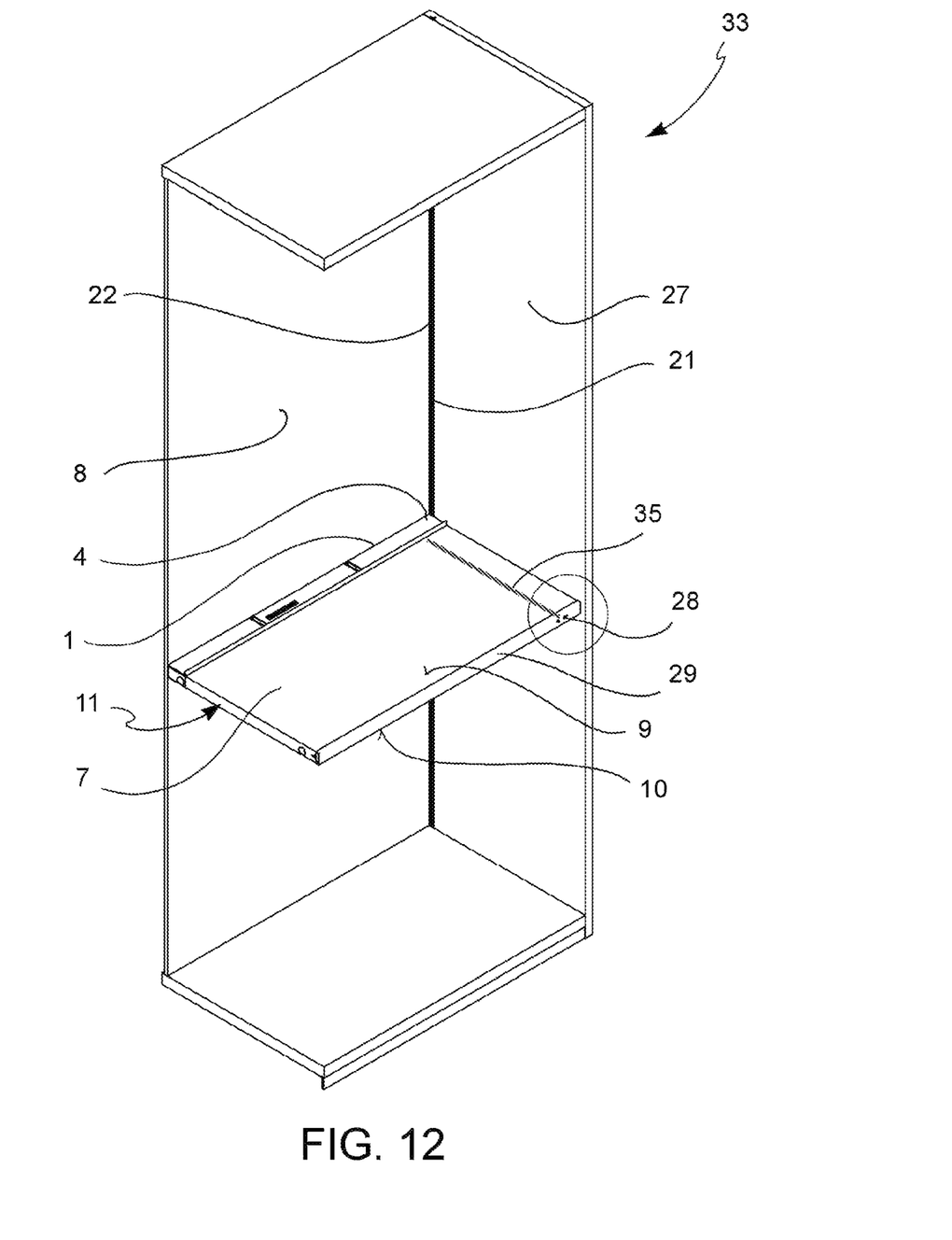
FIG. 12 shows an axonometric view of the structure in FIG. 1, wherein one of the side shoulders was removed to better note the details of the shelf and wherein there is noted the passageway in the shelf for connecting the sanitization device control element arranged in the front edge of the shelf.
Figure 13:
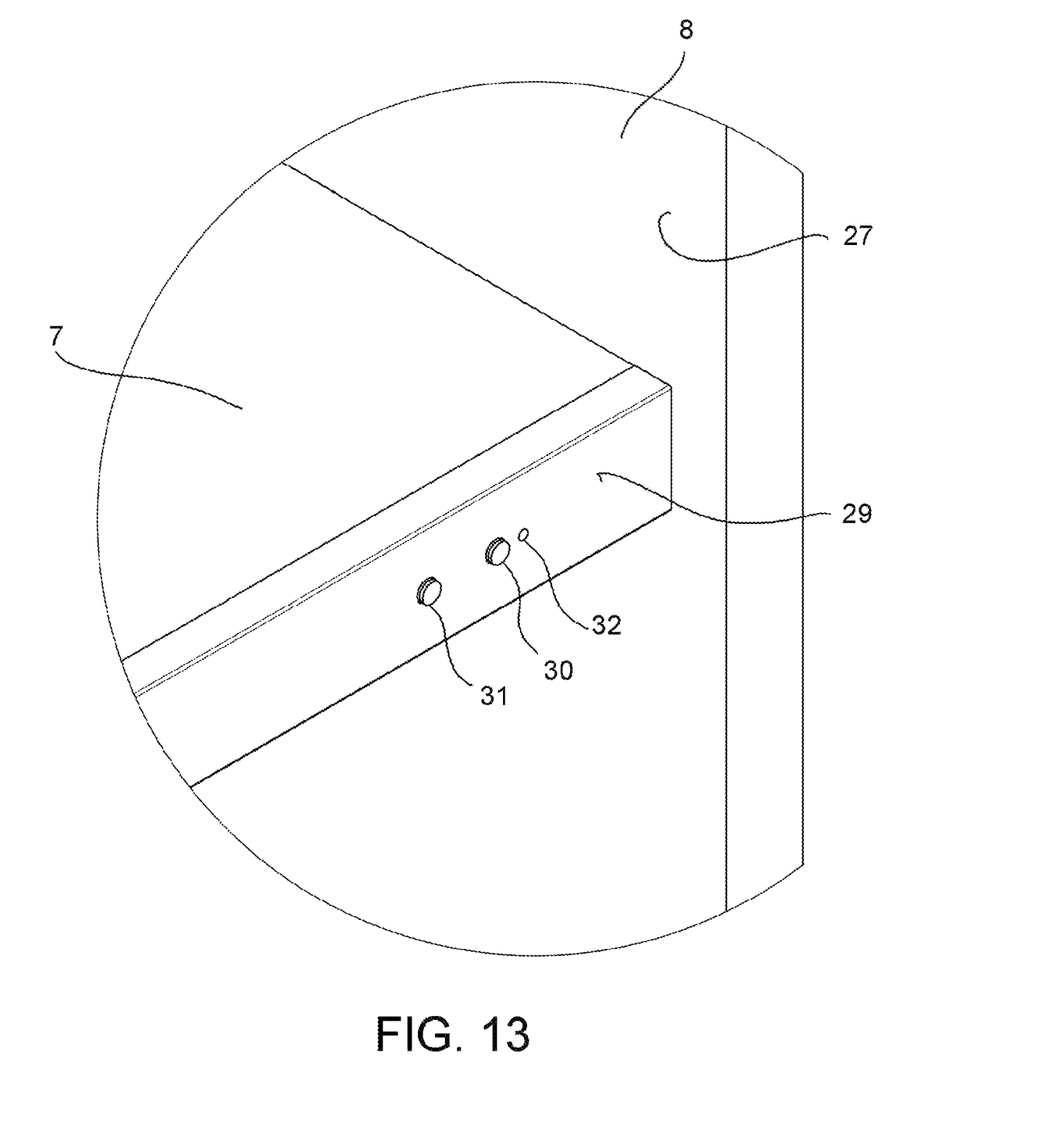
FIG. 13 shows a detail of FIG. 12 noting the controls and the indicator of the sanitization device control element arranged in the front edge of the shelf.

The term "vertical" means a direction but also a vertical plane, i.e. a direction or a plane which is perpendicular or substantially perpendicular to a support surface, for example a floor, on which a furnishing element is resting.

The term "horizontal" means a direction but also a horizontal plane, i.e. a direction or a plane which is transverse to said vertical direction.

The term "sanitization device" means a device capable of sanitizing the air crossing it or the items, such as for example garments and the like, that this sanitized air reaches leaving said device.

The term "air to be sanitized" means air which is inside a compartment, for example the air in a wardrobe or similar furnishing element, for example air which is in contact with garments or the like.

The term "sanitized air" means air which has passed through a sanitization device.

The term "garments" means clothing, shoes, but also items such as handbags, hats, scarves, ties, blankets, pillows, towels and linen in general, or the like.

The term "box-like body" means a structure having a casing which delimits an internal space adapted to contain a sanitization device and which simultaneously is adapted to be associated with a panel or rack or shelf, for example an edge thereof.

The term "upwards" means a direction directed according to the vertical direction and oriented moving away from the support surface, for example a floor, on which a furnishing element is resting.

The term "downwards" means a direction directed according to the vertical direction and oriented approaching the support surface, for example a floor, on which a furnishing element is resting.

The term "electrified tracks" means elongated conductor elements adapted to be recessed in a panel and to feed electric apparatuses in a distributed manner, thus avoiding the use of a point-to-point wiring.

The term "continuing surfaces" means the side-by-side surfaces which avoid creating apparent corners or steps, for example two side-by-side and coplanar surfaces.

In accordance with a general embodiment, a sanitization assembly 1 comprises a sanitization device 2 such as, for example a photocatalytic device or ionizer or the like.

Said assembly further comprises a containment element 3.

Said sanitization device 2 is received in said containment element 3.

Said containment element 3 comprises a box-shaped, box-like containment body 4.

Said box-like containment body 4 comprises side containment body surfaces 9, 10, 11, for example an upper side surface 9, a lower side surface 10 and edge side surfaces or side containment body surfaces 11.

Said box-like containment body 4 has predefined dimensions in the width 5 and thickness 6 thereof. Said width 5 and thickness 6 substantially are identical to those of a panel or rack or shelf 7 of a furnishing element 8.

Said panel or rack or shelf 7 comprises side shelf surfaces 12, 13, 14, for example an upper shelf surface 12, a lower shelf surface 13 and a shelf edge or side shelf surface 14.

Said box-like containment body 4 is assembled on said panel or rack or shelf 7, being continuous with said panel or rack or shelf 7. Said box-like containment body 4 is assembled on said panel or rack or shelf 7 so that the side shelf surfaces 12, 13, 14 substantially continue in said side containment body surfaces 9, 10, 11.

In accordance with an embodiment, said box-like containment body 4 comprises an upper side containment body surface 9, which faces upwards in a normal installation of a furnishing element 8, i.e. in a vertical direction moving away from a support surface of the furnishing element 8.

In accordance with an embodiment, said box-like containment body 4 comprises a lower side containment body surface 10, which faces downwards in a normal installation of a furnishing element 8, i.e. in a vertical direction approaching a support surface of the furnishing element 8.

In accordance with an embodiment, said box-like containment body 4 comprises at least one inlet opening 15 for the air to be sanitized.

In accordance with an embodiment, said box-like containment body 4 comprises at least a first sanitized air outlet opening 16 placed in said upper side containment body surface 9.

In accordance with an embodiment, said box-like containment body 4 comprises at least a second sanitized air outlet opening 17 placed in said lower side containment body surface 10.

In accordance with an embodiment, said box-like containment body 4 comprises a section bar-like body portion 18 obtained from an extruded section bar, for example made of aluminum.

In accordance with an embodiment, said box-like containment body 4 comprises a pair of end caps 19, 20 geometrically connected to the ends of said section bar-like body portion 18.

In accordance with an embodiment, at least one of said end caps 19 comprises electrical connector pins 21, 22 for the electric connection of the sanitization device 2.

In accordance with an embodiment, said electrical connector pins 21, 22 are adapted to cooperate with electrified tracks 23, 24 provided in said furnishing element 8.

In accordance with an embodiment, said end caps 19 comprise shelf support elements 25, 26 for connecting said shelf 7 to a shoulder 27 of the furnishing element 8.

The present invention also relates to a furnishing element shelf 7, wherein said shelf 7 comprises side shelf surfaces 12, 13, 14.

A sanitization assembly 1 according to any one of the preceding embodiments is connected to said shelf 7.

The box-like containment body 4 of said sanitization assembly 1 is connected to said shelf 7, thus being continuous with said shelf 7.

The side shelf surfaces 12, 13, 14 substantially continue in said side containment body surfaces 9, 10, 11.

In accordance with an embodiment, said sanitization assembly 1 is associated with the rear edge of the panel forming the front part of said shelf 7.

In accordance with an embodiment, said shelf comprises at least one control element 28 arranged on a surface which can be accessed by a user and operatively connected to said sanitization device 2 for the operating controls of said sanitization device 2.

In accordance with an embodiment, said shelf 7 comprises a front shelf edge 29 adapted to face a user.

In accordance with an embodiment, a passageway or channel or hole 35 crosses said shelf from the rear edge thereof where said sanitization assembly 1 is associated with said front edge 29 or close thereto, to create a connecting passageway between the sanitization device 2 and a control or control element 28 thereof.

In accordance with an embodiment, said control element 28 is associated with said front shelf edge 29.

In accordance with an embodiment, said control element 28 is recessed in said front shelf edge 29, thus causing only control buttons 30, 31 and at least one status indicator 32 to protrude.

In accordance with an embodiment, at least one of said control buttons 30 is an ON/OFF switch.

In accordance with an embodiment, at least one of said control buttons 30 is a control for adjusting the operating time of the sanitization device 2 or a control for a timer.

In accordance with an embodiment, said status indicator 32 is a status light, for example an LED.

In accordance with an embodiment, said status light is a light indicating the type of operation or operating anomalies of the sanitization device 2.

In accordance with an embodiment, said control element 28 comprises a remote control adapted to receive commands from a remote control remotely operated by a user.

In accordance with an embodiment, a raised edge 36 is provided where the box-like containment body 4 of the sanitization assembly 1 is connected to shelf 7. Said raised edge is useful for containing the garments resting on shelf 7, thus avoiding them from accidentally obstructing the at least one sanitized air outlet opening 16 facing shelf 7 at the top.

The present invention also relates to a furnishing element 8, wherein said furnishing element comprises at least one shelf 7 as defined in any one of the above embodiments.

In accordance with an embodiment, said furnishing element 8 comprises at least one pair of electrified channels or electrified tracks 23, 24.

In accordance with an embodiment, said shelf 7 comprises at least one pair of electrical connector pins 21, 22 which operatively connect to the sanitization device 2 and operatively connect to said electrified tracks 23, 24.

In accordance with an embodiment, said furnishing element 8 comprises at least one furnishing element shoulder 27, wherein said furnishing element shoulder 27 at least partially supports said at least one shelf 7 and wherein said pair of electrified channels or electrified tracks 23, 24 is accommodated in said furnishing element shoulder 27.

In accordance with an embodiment, said furnishing element 8 comprises at least two opposed furnishing element shoulders 27, wherein said two furnishing element shoulders 27 support said at least one shelf 7 and wherein said pair of electrified channels or electrified tracks 23, 24 is accommodated in at least one of said two furnishing element shoulders 27.

In accordance with an embodiment, said at least one shelf 7 is supported by said two opposed furnishing element shoulders 27 in a selectively adjustable manner in various positions thereof while always keeping an operating connection between said pair of electrical connector pins 21, 22 and said electrified tracks 23, 24.

In accordance with an embodiment, said at least one shelf 7 is a shelf or rack or a resting surface of a wardrobe 33.

In accordance with an embodiment, said wardrobe 33 is a furnishing element 8 which can be closed by at least one shutter or door.

In accordance with an embodiment, said at least one shelf 7 comprises at least one lamp bulb 34.

In accordance with an embodiment, said at least one shelf 7 comprises shelf support elements 25, 26 configured as built-in shelf-support couplings, which are recessed in the side edge of said shelf 7.

In accordance with an embodiment, all the shelves 7 of the furnishing element 8 comprise a sanitization assembly 1 according to any one of claims 1 to 3.

The present invention further relates to a method for sanitizing a compartment of a furnishing element 8.

A method for sanitizing a compartment of a furnishing element 8, comprising the steps of:
providing a furnishing element according to any one of the embodiments described above;
taking in air from below the shelf 7;
sanitizing the intake air by means of the sanitization device 2;
discharging the sanitized air both from above the shelf 7 and from below the shelf 7.

Those skilled in the art may make many changes and adaptations to the embodiments described above or can replace elements with others which are functionally equivalent in order to meet contingent and specific needs without however departing from the scope of the appended claims.

LIST OF REFERENCES

1 Sanitization assembly
2 sanitization device
3 containment element
4 box-like containment body
5 width of box-like containment element
6 thickness of box-like containment element
7 panel or rack or shelf
8 furnishing element
9 side containment body surfaces—upper surface
10 side containment body surfaces—lower surface
11 side containment body surfaces—side surface
12 side shelf surfaces—upper surface
13 side shelf surfaces—lower surface
14 side shelf surfaces—side surface
15 inlet opening for the air to be sanitized
16 first sanitized air outlet openings
17 second sanitized air outlet openings
18 section bar-like body portion
19 end cap—cap with electrical connector pins
20 end cap
21 electrical connector pins
22 electrical connector pins
23 electrified tracks
24 electrified tracks
25 shelf support elements
26 shelf support elements
27 furnishing element shoulder
28 sanitization device control element
29 front shelf edge
30 control buttons—ON/OFF
31 control buttons—time adjustment or control for a timer
32 status light—LED—light indicating the operating type or operating anomalies
33 wardrobe
34 lamp bulb

The invention claimed is:
1. A furnishing element, wherein said furnishing element comprises a compartment and a furnishing element shelf positioned in said compartment, said furnishing element shelf comprising side shelf surfaces and a rear shelf edge,
  wherein said furnishing element further comprises a sanitization assembly connected to said furnishing element shelf, said sanitization assembly comprising:
    a box-like containment body that is connected to and continuous with said furnishing element shelf, said box-like containment body comprising side surfaces, wherein said box-like containment body has a width and thickness that are the same as a width and thickness of said furnishing element shelf, and wherein said side shelf surfaces of said furnishing element shelf are continuous with the side surfaces of said box-like containment body; and
    a sanitization device, wherein the sanitization device is a device capable of sanitizing the air crossing it and items that the sanitized air subsequently reaches, and wherein said sanitization device is received in said box-like containment body,
  wherein said sanitization assembly is connected to said furnishing element shelf by connecting to said rear shelf edge of said furnishing element shelf, said furnishing element shelf and said sanitization assembly being co-planar with one another;
  wherein the side surfaces of said box-like containment body include:
    an upper side containment body surface, which faces upwards in a normal installation of the furnishing element, in a vertical direction moving away from a support surface of the furnishing element; and
    a lower side containment body surface, which faces downwards in the normal installation of the furnishing element, in the vertical direction approaching the support surface of the furnishing element; and
  wherein said box-like containment body further comprises at least one inlet opening for the air to be sanitized, at least a first sanitized air outlet opening defined in said upper side containment body surface, and at least a second sanitized air outlet opening defined in said lower side containment body surface.

2. The furnishing element according to claim 1, wherein:
  said box-like containment body further comprises a section bar-like body portion obtained from an extruded section bar; and
  said box-like containment body further comprises a pair of end caps geometrically connected to ends of said section bar-like body portion;
wherein:
  at least one of said end caps comprises electrical connector pins for electric connection of said sanitization device;
wherein:
  said electrical connector pins are adapted to cooperate with electrified tracks provided in the furnishing element; and
wherein:
  said end caps comprise shelf support elements for connecting the furnishing element shelf to a shoulder of the furnishing element.

3. The furnishing element according to claim 1, wherein:
  said furnishing element shelf further comprises at least one control element arranged on a surface accessible to a user and operatively connected to the sanitization device for operating controls of the sanitization device;
wherein:
  said furnishing element shelf further comprises a front shelf edge adapted to face the user; and
  said at least one control element is associated with said front shelf edge; said at least one control element is recessed in said front shelf edge, thus causing only control buttons and at least one status indicator to protrude.

4. The furnishing element according to claim 1, wherein:
  said furnishing element further comprises at least one pair of electrified channels or electrified tracks; and
  said furnishing element shelf comprises at least one pair of electrical connector pins that operatively connect to the sanitization device and operatively connect to said electrified tracks.

5. The furnishing element according to claim 1, wherein:
  said furnishing element shelf comprises shelf support elements configured as built-in shelf-support couplings, which are recessed in a side edge of said furnishing element shelf.

6. A method for sanitizing a compartment of a furnishing element, the method comprising the steps of:
  providing a furnishing element according to claim 1;
  taking in air from below the furnishing element shelf;
  sanitizing the intake air by means of the sanitization device; and
  discharging the sanitized air both from above the furnishing element shelf and from below the furnishing element shelf reaching said compartment of the furnishing element from behind.

7. The furnishing element of claim 1, wherein the sanitization device comprises a photocatalytic device or ionizer.

8. The furnishing element of claim 2, wherein said extruded section bar is made of aluminum.

9. The furnishing element according to claim 3, wherein said status indicator is an LED.

10. The furnishing element according to claim 3, wherein at least one of said control buttons is a control for adjusting an operating time of the sanitization device or a control for a timer.

11. The furnishing element according to claim 3, wherein said status indicator is a status light and said status light is a light indicating a type of operation or operating anomalies of the sanitization device.

12. The furnishing element according to claim 3, wherein said at least one control element comprises a remote control adapted to receive commands from a remote control remotely operated by the user.

13. The furnishing element according to claim 11, wherein said status light is an LED.

14. The furnishing element according to claim 4, wherein said furnishing element further comprises at least two opposed furnishing element shoulders, wherein said at least two furnishing element shoulders support said furnishing element shelf, wherein said pair of electrified channels or electrified tracks is accommodated in at least one of said at least two furnishing element shoulders, and wherein said furnishing element shelf is supported by said at least two opposed furnishing element shoulders in a selectively adjustable manner in various positions thereof while always keeping an operating connection between said pair of electrical connector pins and said electrified tracks.

* * * * *